United States Patent [19]
Peel et al.

[11] Patent Number: 4,803,996
[45] Date of Patent: Feb. 14, 1989

[54] CARDIOVASCULAR MONITOR

[75] Inventors: H. Herbert Peel, San Antonio; Merle E. Converse, Helotes; William H. McGinnis, San Antonio; Donald J. Shirley, Boerne; John P. Prudhomme, Converse, all of Tex.

[73] Assignee: Nippon Colin Co., Ltd., Komaki, Japan

[21] Appl. No.: 101,812

[22] Filed: Sep. 28, 1987

[51] Int. Cl.[4] .............................................. A61B 5/04
[52] U.S. Cl. .................................. 128/710; 128/696; 128/715
[58] Field of Search ............... 128/710, 696, 695, 706, 128/715, 901

[56] References Cited

U.S. PATENT DOCUMENTS

| | | | |
|---|---|---|---|
| 3,442,264 | 5/1969 | Levitt | 128/2.06 |
| 3,565,058 | 2/1971 | Mansfield | 128/2.06 |
| 3,650,264 | 3/1972 | Janssen | 128/2.06 |
| 3,690,313 | 9/1972 | Weppner et al. | 128/696 |
| 3,732,868 | 5/1973 | Willems et al. | 128/2.06 |
| 3,760,100 | 9/1973 | Raggdale et al. | 179/1 R |
| 3,830,227 | 8/1974 | Green | 128/2.06 |
| 3,858,034 | 12/1974 | Anderson | 235/151.3 |
| 3,908,641 | 9/1975 | Judson et al. | 128/710 |
| 4,203,451 | 5/1980 | Panico | 128/672 |
| 4,364,397 | 12/1982 | Citron et al. | 128/710 |
| 4,417,306 | 11/1983 | Citron et al. | 364/415 |
| 4,425,922 | 1/1984 | Conti et al. | 128/696 |
| 4,450,527 | 5/1984 | Sramek | 364/415 |
| 4,506,678 | 3/1985 | Russell et al. | 128/696 |
| 4,576,178 | 3/1986 | Johnson | 128/670 |
| 4,630,204 | 12/1986 | Mortara | 128/901 |
| 4,679,570 | 7/1987 | Lund et al. | 128/715 |

Primary Examiner—Francis J. Jaworski
Assistant Examiner—George Manuel
Attorney, Agent, or Firm—Gunn, Lee & Jackson

[57] ABSTRACT

A cardiovascular monitor having improved safety features and data transmission ability. Sensing devices placed on a patient's body, such as electrocardiogram electrodes and phonocardiogram microphones, are electrically isolated from the data recorder and AC powerline, thereby protecting the patient from dangerously high voltages existing in the recorder and the external power source. Isolation amplifiers are employed in the signal conditioning circuitry at the front end of the recorder. Special isolation transformers are also used to prevent ground loop currents between the signal conditioner and the recorder thus minimizing noise due to powerline leakage. Similarly, isolation amplifiers are used during the playback mode between the recorder and a data processor to avoid ground loop currents between the recorder and the processor.

5 Claims, 2 Drawing Sheets

CARDIOVASCULAR MONITOR

BACKGROUND OF THE INVENTION

1. Field of the Invention

The present invention generally relates to devices for monitoring the heart and surrounding blood vessels, and more particularly to such a device which provides improved signal conditioning.

2. Description of the Prior Art

Every year, more than 550,000 people die of heart attacks in the United States alone. In fact, heart disease is the number one killer of persons living in the U.S. Heart attacks are usually brought on by the accumulation of fat and other substances within the coronary arteries, those vessels which supply the heart itself with oxygen and nutrient-rich blood.

Research scientists are getting closer to the secret of preventing heart attacks. The most important aspect of prevention is detecting the presence of arteriosclerosis before it advances to a critical stage. There are many instruments currently in use for invasive and noninvasive measurement of various cardiac parameters. Techniques include ballistocardiography, electrical impedance measurements, ultrasonics, and vibrocardiography. The present invention is more related to traditional cardiac monitoring using electrocardiograms (ECG) and phonocardiograms (PCG).

The ECG signals resulting from the electrical activity of the cardiac muscle are extremely valuable diagnostic indicators when viewed by an experienced cardiologist. Certain abnormalities in these signals can be indicative of different types of heart disorders. Similarly, acoustic patterns taken via PCG may also provide useful information. The difficulty in recording this data, however, lies in the fact that stray electrical potentials can distort the measurements and obscure useful information hidden in the instrumentation output. Signals in analog form are often recorded on magnetic tape, then reproduced at a later time for conversion to digital form for processing. When the connection is made between the recorder output and the processing equipment, powerline noise can be introduced, in addition to circulating electric currents in ground loops.

Another problem arises in placement of the electrodes or transducers on the human body. Any such devices should have a high degree of isolation from the AC powerline and from the powerline ground for safety reasons. Commercially available magnetic tape recorders do not have the required input circuit isolation. Thus, the recorders cannot be connected directly to the electrodes or transducers, creating further potential for signal loss.

Finally, even if the signals could be recorded without distortion, it has been found that certain low-frequency components of the acoustic signal having a relatively large amplitude tend to drown out the higher-frequency components. Much vital diagnostic information is thereby lost.

It would, therefore, be desirable and advantageous to devise a system for monitoring the ECG and PCG of the heart whereby excessive external noise is minimized. The system should allow for connection of the recorder to the electrodes and transducers without introducing ground loop currents, and should also provide a means of preserving high-frequency acoustic signals for later processing.

SUMMARY OF THE INVENTION

Accordingly, the primary object of the present invention is to provide a monitoring system which accurately records electrical and acoustical signals from the heart.

Another object of the invention is to provide such a system which has a high degree of isolation between the AC powerline and the electrodes attached to the patient.

Yet another object of the invention is to provide a monitoring system which prevents ground loop currents between recording and processing units.

Still another object of the invention is to provide a cardiovascular monitor capable of supplying electrical and acoustical signals to a recorder in such a fashion that high-frequency components of the acoustical signal are not over-powered by the larger amplitude low-frequency components.

The foregoing objects are achieved in a cardiovascular monitor having a signal conditioner, a conventional recorder, and a recorder/processor interface unit. The signal conditioner isolates the ECG and PCG signals from the recording unit and further modifies the acoustical signal into separate low- and high-frequency channels. Both the signal conditioner and the recorder/processor interface unit employ isolation amplifiers and isolation transformers having extensive shielding and filtering.

BRIEF DESCRIPTION OF THE DRAWINGS

The novel features believed characteristic of the invention are set forth in the appended claims. The invention itself, however, as well as a preferred mode of use, further objects and advantages thereof, will best be understood by reference to the following detailed description of illustrative embodiments when read in conjunction with the accompanying drawings, wherein:

DESCRIPTION OF THE PREFERRED EMBODIMENTS

Figure 1:
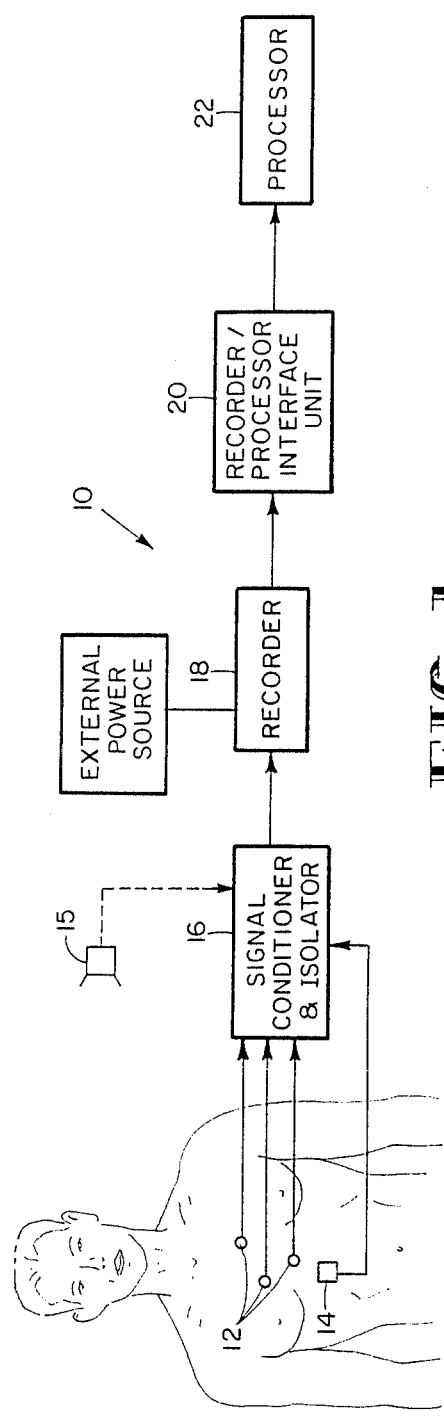
FIG. 1 is a block diagram showing the general components of the cardiovascular monitoring system.

With reference now to the figures, and in particular with reference to FIG. 1, there is depicted a block diagram showing the general arrangement of cardiovascular monitor 10. Cardiovascular monitor 10 is generally comprised of electrocardiogram electrodes 12, phonocardiogram microphone 14, signal conditioner and isolater 16, recorder 18, interface unit 20, and processor 22. ECG electrodes are known in the art. PCG microphones are also known, and generally have piezoelectric crystals which pick up internal acoustical activity. The inventors prefer using a PCG microphone having transducers with a 0.01 microfarad capacitance per element.

ECG electrodes 12 are placed on the body along with PCG microphone 14. An acoustic microphone 15 may optionally be used for filtering out ambient noise occurring during recording. The inventors have used model numbers SM11 and SM11CN manufactured by Shure Electronics. The leads from ECG electrodes 12 and PCG microphone 14 are connected to signal conditioner/isolator 16 which prepares the signals for recorder 18. Input protection resistors are usually employed in connecting the leads, having around a 1 watt rating and 100 kilo-ohm resistance. Recorder 18 is a conventional magnetic tape recorder, such as that manufactured by Racal of Irvine, Calif., under the trade name STOREHORSE, and is powered by a standard 120 volt AC powerline. In playback mode, recorder 18 outputs the recorded signal to a recorder/processor interface unit 20 which further conditions the signal for input into the data processor 22. Processor 22 typically converts the analog signal to digital form and performs any one of a number of data analysis functions on the digital data. The present invention does not concern itself with the processing of the extracted information.

Figure 2:
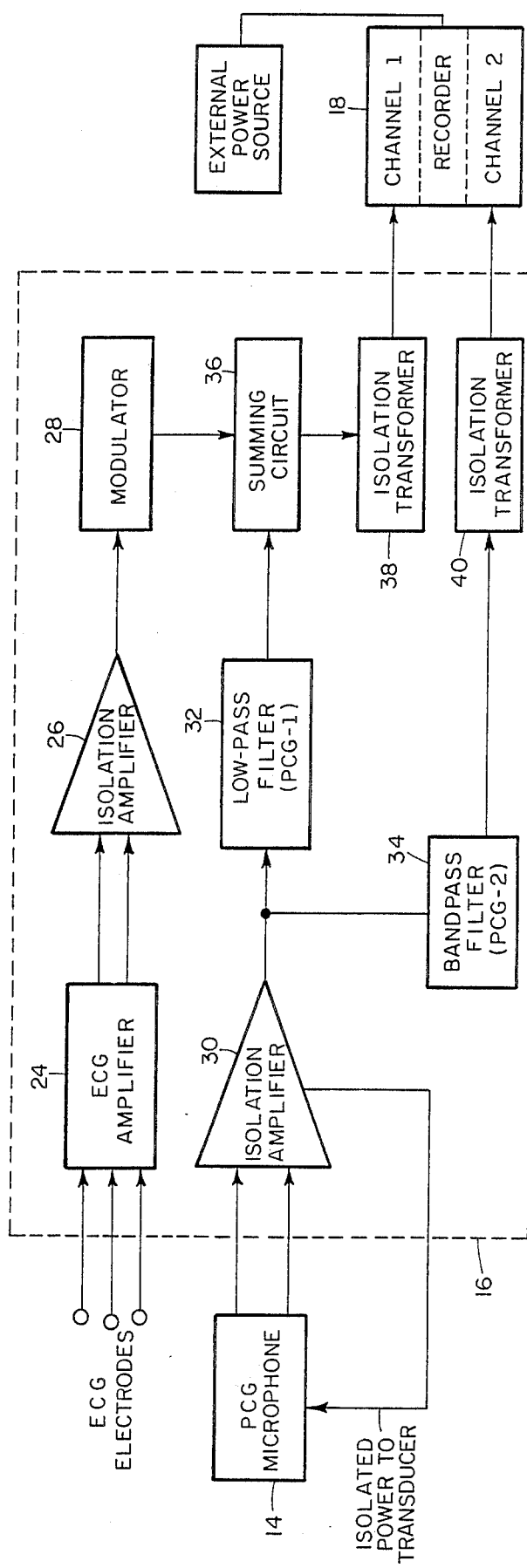
FIG. 2 is a schematic of the signal conditioner of the present invention.

The design of signal conditioner 16 is further illustrated in FIG. 2. Cables from ECG electrodes 12 are connected to the input of an ECG amplifier 24. This circuit converts the three-wire raw input signal to a two-wire output signal. ECG amplifiers are known, and a suitable unit may be purchased from the Hewlett Packard Co. ECG amplifier 24 should incorporate low leakage input amplifiers. These wires are then connected to the input of an isolation amplifier 26.

Isolation amplifier 26 provides protection against powerline leakage and converts the raw ECG signal into a single-ended isolated output signal having a common connection to the signal conditioner ground. Isolation amplifiers are familiar to those skilled in the art. They generally provide full isolation between input, output, and power supply ports. Thus, the patient is properly protected from surges or breakdowns in signal conditioner 16 or recorder 18. Isolation amplifier 26 should have a high input impedance (about 100 mega ohms), input voltage ratings of at least 10 volts (differential range), and a rated output of $\pm 10$ volts on a 2000 ohm load. A power supply of 15 volts DC is usually required. The inventors have found that the isolation amplifier manufactured by Analog Devices of Norwood, Mass., under model No. AD295, is preferable. The present invention therefore provides a high degree of isolation between the patient and the DC powerline.

The single-ended ECG signal is applied to the control input of a voltage-controlled oscillator or modulator 28 to produce a frequency-modulated (FM) signal. A center frequency of about 7 kHz with a deviation of $\pm 2$ kHz has been found satisfactory for this purpose. The modulated ECG signal is then combined with the PCG signal in a resistive summing circuit (described below).

The leads from PCG microphone 14 are connected to the input of another isolation amplifier 30, identical to amplifier 26, which again protects against powerline leakage and converts the raw PCG signal to a single-ended output having a common connection to the signal conditioner ground. The isolated power port of amplifier 30 provides voltage to the transducer (not shown) in microphone 14. The isolated PCG signal is then divided into two circuit paths or limited signals, according to the frequency ranges desired. It has empirically been found that frequencies in the range of 100 to 1000 Hz contain important information on the condition of the coronary arteries; this bandwidth is difficult to analyze if lower-frequency components (i.e., below 100 Hz) are included, as the low-frequency components are relatively large in amplitude. Therefore, the PCG signal is routed to both low-pass filter 32 (PCG1) and band-pass filter 34 (PCG2).

Low-pass filter 32 passes signal frequencies below 1000 Hz, attenuating high frequency noise. Generally, the lowest frequency signal from the PCG microphone is about 20 Hz. The gain of this channel is set low enough to avoid overloading due to the large amplitude low-frequency components. Where noise above 1000 Hz is negligible, low-pass filter 32 is unnecessary. This channel is then coupled with the modulated ECG signal from modulator 28 in summing circuit 36. As one skilled in the art will appreciate, many conventional recorders have only two channels, so recordation of three different signals (ECG, PCG1, and PCG2) requires multiplexing. The inventors prefer to multiplex the signals by frequency division, using modulator 28 and summing circuit 36. The multiplexed signal then passes through isolation transformer 38 to the first channel of recorder 18. Of course, if a 4-channel or 16-channel recorder is used, multiplexing is not necessary.

Isolation transformer 38 is a high-impedance transformer responsive to frequencies between 20 and 1000 Hz. The tranformer must be balanced to insure proper transmission of the multiplexed signal. The inventors prefer to use the transformer made by TRW-UTC Transformers of New York, N.Y., model No. 0-26.

The portion of the PCG signal lying within the range of 100 to 1000 Hz (PCG2) passes through bandpass filter 34, which attenuates signal components at frequencies below 100 Hz. Filter 34 may alternatively be a high-pass filter. The signal then passes through isolation transformer 40 to the second channel of recorder 18. Isolation transformer 40 is identical to transformer 38. The PCG2 channel must be maintained at high quality and high dynamic range as this signal is used in the data processor 22 to correlate the acoustic heart signals with the medical condition of the heart. Isolation transformers 38 and 40 prevent ground loop currents between signal conditioner 16 and recorder 18 which could adulterate the PCG and ECG signals.

Figure 3:
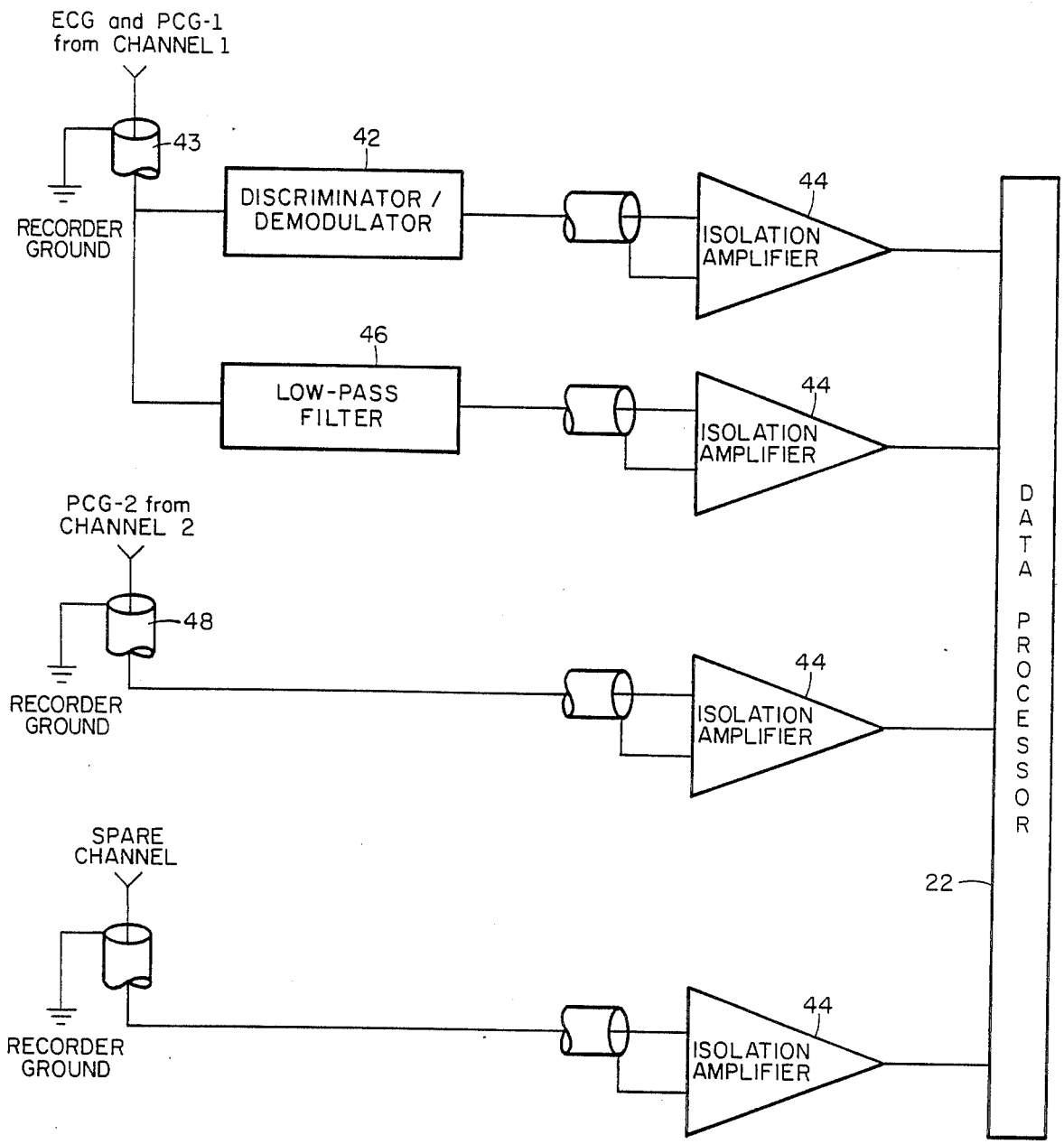
FIG. 3 is a schematic of the recorder/processor interface unit of the present invention.

After recording the ECG and PCG information, the data may be played back into data processor 22 at a later time. This is accomplished by means of recorder/processor interface unit 20. Recorder/processor interface unit 20 is shown in more detail in FIG. 3. The combined ECG and PCG1 signal from the first channel of recorder 18 is coupled to discriminator 42 by coaxial cable 43 having a common connection to the ground of recorder 18, whereby the FM signal is demodulated to recover the ECG signal. The separated ECG signal is then output to processor 22, via isolation amplifier 44. Processor 22 should have at least three input ports. Isolation amplifier 44 is identical to amplifiers 26 and 30, and prevents powerline noise or ambient currents from flowing on the shields of the input cables. A low impedance output is provided to drive the cables connecting the amplifier output to the data processor unit 22. Although amplifiers 44 and processor 22 are separately connected to the AC powerline, the inventors have found that ground loop currents flowing therebetween are negligible.

Signals from channel 1 of recorder 18 are also applied to the input of another low-pass filter 46. This filter attenuates the frequency components above 1000 Hz, eliminating the ECG FM signal. The PCG1 signal in the frequency range of 20 to 1000 Hz is passed to another isolation amplifier 44 and then to processor 22.

The PCG2 signal is also passed to processor 22 via a third isolation amplifier 44. As with the channel 1 signal, the PCG2 signal travels in a coaxial cable 48 having a common connection to the ground of recorder 18. Finally, a spare channel is provided for other signals, such as the signal from an acoustic microphone which may be used in conjunction with the PCG microphone 14. The acoustic microphone (not shown) could be used to identify ambient noise in the room in which the other measurements are taken.

As an alternative embodiment of the present invention, the signal conditioner 16 and/or recorder/processor interface unit 20 could be manufactured integrally with recorder 18. In this embodiment, isolation amplifiers 26 and 30 would provide output signals having common connections to the recorder ground. Also, isolation transformers 38 and 40 would be unnecessary as there would be no ground loop currents. It should further be understood that interface unit 20 may be used for any recorder/processor system and not just those dealing with cardiovascular monitoring.

Although the invention has been described with reference to specific embodiments, this description is not meant to be construed in a limiting sense. Various modifications of the disclosed embodiment, as well as alternative embodiments of the invention will become apparent to persons skilled in the art upon reference to the description of the invention. It is therefore contemplated that the appended claims will cover such modifications that fall within the true scope of the invention.

We claim:

1. A device for monitoring acoustical and electrical indicia of the heart and coronary artery activity of a patient as measurable through electrocardiogram and phonocardiogram means, comprising:

sensing means comprising a plurality of electrocardiogram electrodes which, when placed on said patient for monitoring said activity and electrically connected to a source of electrical power for operation of said electrodes, each produce a primary ECG analog signal representative of electrical potentials resultant of said activity.

said sensing means further comprises a phonocardiogram microphone which, when operably placed on said patient, produces a primary PCG analog signal in response to acoustically measurable indicia of said patient's cardiac activity;

recording means comprising a magnetic tape recorder having first and second input means for receiving and recording analog signals on first and second channels of magnetic recording tape and first and second output means for transmitting recordation of said analog signals respectively on said first and second channels to signal processing means; and means for electrically isolating said electrodes from said recording means whereby said patient is protected from dangerously high voltages existing in said recording means and from sources of electrical power associated with said recording means, said electrode isolating means comprising a first isolation amplifier, said primary ECG analog signals produced by said electrodes being fed to said first isolation amplifier in response to which said first isolation amplifier produces isolated secondary ECG analog signals corresponding to said primary ECG analog signals in frequency and amplitude values, said secondary ECG analog signals being conducted to said recording means solely through said recording means' electrical connection with said first isolation amplifier;

means for electrically isolating said microphone from said recording means whereby said patient is protected from dangerously high voltages existing in said recording means and from sources of electrical power associated with said recording means, said microphone isolating means comprising a second isolation amplifier, said primary PCG analog signal produced by said microphone being fed to said second isolation amplifier in response to which said second isolation amplifier produces an isolated secondary PCG analog signal corresponding to said primary PCG analog signal in frequency and amplitude values, said secondary PCG analog signal being conducted to said recording means solely through said recording means' electrical connection with said second isolation amplifier;

signal conditioning means for conditioning said secondary analog signals prior to transmission to said input means of said recording means comprising:

modulator means electrically connected to said first isolation amplifier which produces said secordary ECG analog signals for converting said secondary ECG analog signals into a frequency modulated signal, a first low-pass filter means electrically connected to said second isolation amplifier which produces said secondary PCG analog signal for producing a first limited signal from said secondary PCG analog signal, said first limited signal being the frequency band of said secondary PCG analog signal with frequencies less than approximately 1000 Hertz, bandpass filter means electrically connected to said second isolation amplifier which produces said secondary PCG analog signal for producing a second limited signal, said second limited signal being the frequency band of said secondary PCG analog signal lying in the frequency range of approximately 100 to 1000 Hertz, and means for summing said frequency modulated signal and said first limited signal, thereby producing a combined signal for recording on said first channel by said recorder, input ports of said summing means being electrically connected with said modulator and with said low pass filter and an output port of said summing means being electrically connected to said first channel of said recorder, said bandpass filter being electrically connected with said second channel of said recorder whereby said second limited signal is recorded on said second channel of said recorder; and means for preventing ground loop currents between said signal conditioning means and said recording means, said preventing means comprising one or more isolation transformers providing sole electrical connections for conveying signals from said signal conditioning means to said recording means.

2. The device of claim 1 wherein said first and second output means of said recorder are electrically connected to said signal processor by means of a recorder/processor interface unit, said interface unit comprising:

discriminator/demodulator means electrically connected to said first output means of said recorder for receiving playback of recordings of data recorded on said first channel, said discriminator/demodulator means for separating said frequency modulated signal from said combined signal and demodulating said frequency modulated signal to reproduce said secondary ECG analog signal;

second low-pass filter means electrically connected to said first output of said recorder for receiving playback of recordings of data recorded on said first channel for separating said first limited signal from said combined signal;

a third isolation amplifier electrically connected to said discriminator/demodulator and said processor, for preventing powerline interference with said ECG signal;

a fourth isolation amplifier electrically connected to said second low-pass filter and said processor for preventing powerline interference with said first limited signal; and a fifth isolation amplifier electrically connected to a second output of said recorder for receiving playback of recordings of said second limited signal recorded on said second channel and conveying said second limited signal to said processor and for preventing powerline interference with said second limited signal.

3. A device for monitoring acoustical and electrical indicia of heart and coronary artery function of a patient as measurable through electrocardiogram and phonocardiogram means, comprising:

a magnetic tape recorder having first and second input means for receiving and recording analog signals on first and second channels of magnetic recording tape and first and second output means for transmitting recordation of said analog signals respectively on said first and second channels to signal conditioning means;

a plurality of electrocardiogram electrodes which, when placed on said patient for monitoring said activity and electrically connected to a source of electrical power for operation of said electrodes, each produce a primary ECG analog signal representative of electrical potentials resultant of said patient's cardiac function;

a phonocardiogram microphone, which when operably placed on said patient, produces a primary PCG analog signal in response to acoustically measurable indicia of said patient's cardiac activity;

an ECG amplifier electrically connected to said electrocardiogram electrodes whereby said primary ECG analog signals are converted into an amplified primary ECG analog signal;

a first isolation amplifier electrically connected to said ECG amplifier for electrically isolating said electrodes from said recorder whereby said patient is protected from dangerously high voltages existing in said recorder and power sources connected to said recorder, said first isolation amplifier converting said amplified primary ECG analog signal into an isolated secondary ECG analog signal identical to said primary ECG analog signal in amplitude and frequency values;

a second isolation amplifier electrically connected to said phonocardiogram microphone for electrically isolating said microphone from said recorder whereby said patient is protected from dangerously high voltages existing in said recorder and said power sources to said microphone, said second isolation amplifier providing isolated power for said microphone and converting said primary PCG analog signal into an isolated secondary PCG analog signal;

a modulator electrically connected to said first isolation amplifier for converting said isolated secondary ECG analog signal into a frequency modulated signal having a center frequency of approximately 7 kHz;

a first low-pass filter electrically connected to said second isolation amplifier for converting said isolated secondary PCG analog signal into a first limited signal, and first limited signal being the frequency band of said isolated secondary PCG analog signal with frequencies less than approximately 1000 Hertz;

a summing curcuit electrically connected to said modulator and said first low-pass filter for combining said frequency modulated signal and said first limited signal into a multiplexed signal;

a first isolation transformer electrically connected to said summing circuit and said first input means of said recorder, said first isolation transformer providing the sole said electrical connection between said summing circuit and said first input means thereby preventing ground loop currents with said recorder;

a bandpass filter electrically connected to said second isolation amplifier for producing a second limited signal, said second limited signal being the frequency band of said isolated secondary PCG analog signal lying in the frequency range of approximately 100 to 1000 Hertz;

a second isolation transformer electrically connected to said bandpass filter and said second input means of said recorder, said second isolation transformer providing the sole said electrical connection between said bandpass filter and said second input means thereby preventing ground loop currents with said recorder;

a signal processor having at least three processor input ports;

discriminator/demodulator means electrically connected to said first output means of said recorder for receiving playback of recordings of data recorded on said first channel, said discriminator/demodulator means for separating said frequency modulated signal from said multiplexed signal and demodulating said frequency modulated signal to reproduce said secondary ECG analog signal;

a third isolation amplifier electrically connected to said discriminator/demodulator and a first one of said at least three input ports of said processor, said third isolation transformer the sole said electrical connection between said discriminator/demodulator and said first one of at least three input ports thereby preventing ground loop currents between said recorder and said processor;

a second low-pass filter electrically connected to said first output means of said recorder for receiving playback of recordings of data recorded on said first channel and by passing only signals of frequencies below approximately 100 Hz providing said processor with a signal comparable in frequency and amplitude with said first limited signal;

a fourth isolation amplifier electrically connected to said second low-pass filter and a second one of said at least three input ports of said processor for, said fourth isolation transformer the sole said electrical connection between said second low pass filter and said second one of at least three input ports and said thereby preventing ground loop currents between said recorder and said processor; and a fifth isolation amplifier electrically connected to said second output means of said recorder and a third one of at least three input ports of said processor, said fifth isolation transformer the sole said electrical connection between said second output means and said third one of at least three input ports thereby preventing ground loop currents between said recorder and said processor.

4. A device for monitoring physical and electrical indicia of the heart and coronary arteries of a patient as measurable through electrocardiogram and phonocardiogram means, comprising:

a plurality of electrocardiogram which, when placed on said patient for monitoring said activity and electrically connected to a first power means for providing electrical power to said electrodes, each produce a primary ECG analog signal representative of electrical potentials resultant of said patient's cardiac function;

an ECG amplifier electrically connected to said electrocardiogram electrodes whereby said primary ECG analog signals are converted into an amplified primary ECG analog signal;

a phonocardiogram microphone which, when operably placed on said patient, produces a primary PCG analog signal in response to acoustically measurable indicia of said patient's cardiac activity;

recording means electrically connected to said ECG amplifier and to said microphone for recording ECG analog signals and PCG analog signals, said recording means comprising a magnetic tape recorder having first and second channels with first and second input means for respectively receiving data for recording on said first and second channels and first and second output means for respectively transmitting said data recorded on said first and second channels;

means for electrically isolating said electrodes and said phonocardiogram microphone from said recorder whereby said patient is protected from dangerously high voltages existing in said recorder and said power means, said electrode isolating means comprising isolation amplifiers for each of said electrode and microphone, said primary ECG and PCG analog signals being input to respective said isolation amplifiers whereby said isolation amplifiers provide isolated secondary ECG and PCG analog signals to said recording means, said isolated secondary analog signals being substantially identical to respective said primary ECG and PCG analog signals in amplitude and frequency values;

signal conditioning means for conditioning said isolated secondary ECG and PCG signals, prior to transmission to said recording means, said conditioning means comprising:

modulator means electrically connected to said isolation amplifiers producing said secondary ECG analog signals for converting said secondary ECG analog signals into a frequency modulated signal;

a first low-pass filter electrically connected to said isolation amplifier producing said secondary PCG analog signal for producing a first limited signal from said secondary PCG analog signal, said first limited signal being the frequency band of said secondary PCG analog signal of frequencies less than approximately 1000 Hertz, bandpass filter means electrically connected to said isolation amplifier producing said secondary PCG analog signal for producing a second limited signal, said second limited signal being the frequency band of said secondary PCG analog signal lying in the frequency range of approximately 100 to 1000 Hertz, and means for summing said frequency modulated signal and said first limited signal, thereby producing a combined signal for recording on said first channel of said recorder, input ports of said summing means being electrically connected with said modulator and with said low pass filter and an output port of said summing means being electrically connected to said first channel of said recorder, said bandpass filter being electrically connected with said second channel of said recorder whereby said second limited signal is recorded on said second channel of said recorder; and means for preventing ground loop currents between said signal conditioning means and said recording means, said preventing means comprising one or more isolation transformers serving as sole electrical connections between said summing means with said first channel and between said bandpass filter with said second channel.

5. A device for monitoring acoustical and electrical indicia of the heart and coronary artery activity of a patient as measurable through electrocardiogram and phonocardiogram means, comprising:

sensing means comprising a plurality of electrocardiogram electrodes which, when placed on said patient for monitoring said activity and electrically connected to a source of electrical power for operation of said electrodes, each produce a primary ECG analog signal representative of electrical potentials resultant of said activity;

said sensing means further comprises a phonocardiogram microphone which, when operably placed on said patient, produces a primary PCG analog signal in response to acoustically measurable indicia of said patient's cardiac activity;

recording means comprising a magnetic tape recorder having first and second input means for receiving and recording analog signals on first and second channels of magnetic recording tape and first and second output means for transmitting recordation of said analog signals respectively on said first and second channels to signal processing means having at least three processor input ports; and means for electrically isolating said electrodes from said recording means whereby said patient is protected from dangerously high voltages existing in said recording means and from sources of electrical power associated with said recording means, said electrode isolating means comprising a first isolation amplifier, said primary ECG analog signals produced by said electrodes being fed to said first isolation amplifier in response to which said first isolation amplifier produces isolated secondary ECG analog signals corresponding to said primary ECG analog signals in frequency and amplitude values, said secondary ECG analog signals being conducted to said recording means solely through said recording means' electrical connection with said first isolation amplifier;

means for electrically isolating said microphone from said recording means whereby said patient is protected from dangerously high voltages existing in said recording means and from sources of electrical power associated with said recording means, said microphone isolating means comprising a second isolation amplifier, said primary PCG analog signal produced by said microphone being fed to said second isolation amplifier in response to which said second isolation amplifier produces an isolated secondary PCG analog signal corresponding to said primary PCG analog signal in frequency and amplitude values, said secondary PCG analog signal being conducted to said recording means solely through said recording means' electrical connection with said second isolation amplifier;

signal conditioning means for conditioning said secondary analog signals prior to transmission to said input means of said recording means comprising:

modulator means electrically connected to said first isolation amplifier which produces said secondary ECG analog signals for converting said secondary ECG analog signals into a frequency modulated signal, a first low-pass filter means electrically connected to said first isolation amplifier which produces said secondary PCG analog signal for producing a first limited signal from said secondary PCG analog signal, said first limited signal being the frequency band of said secondary PCG analog signal with frequencies less than approximately 1000 Hertz, bandpass filter means electrically connected to said first isolation amplifier which produces said secondary PCG analog signal for producing a second limited signal, said second limited signal being the frequency band of said secondary PCG analog signal lying in the frequency range of approximately 100 to 1000 Hertz, and means for summing said frequency modulated signal and said first limited signal, thereby producing a combined signal for recording on said first channel by said recorder, input ports of said summing means being electrically connected with said modulator and with said low pass filter and an output port of said summing means being electrically connected to said first channel of said recorder, said bandpass filter being electrically connected with said second channel of said recorder whereby said second limited signal is recorded on said second channel of said recorder; and means for preventing ground loop currents between said signal conditioning means and said recording means, said preventing means comprising one or more isolation transformers providing sole electrical connections for conveying signals from said signal conditioning means to said recording means.

said first and second output means of said recorder are electrically connected to said signal processor by means of a recorder/processor interface unit, said interface unit comprising:

discriminator/demodulator means electrically connected to said first output means of said recorder for receiving playback of recordings of data recorded on said first channel, said discriminator/demodulator means for separating said frequency modulated signal from said combined signal and demodulating said frequency modulated signal to reproduce said secondary ECG analog signal;

second low-pass filter means electrically connected to said first output of said recorder for receiving playback of recordings of data recorded on said first channel for separating said first limited signal from said combined signal;

a third isolation amplifier electrically connected to said discriminator/demodulator and a first one of said at least three input ports of said processor, said third isolation transformer being the sole said electrical connection between said discriminator/demodulator and said first one of at least three input ports thereby preventing ground loop currents between said recorder and said processor;

a fourth isolation amplifier electrically connected to said second low-pass filter and a second one of said at least three input ports of said processor for, said fourth isolation transformer the sole said electrical connection between said second low pass filter and said second one of at least three input ports and said thereby preventing ground loop currents between said recorder and said processor;

a fifth isolation amplifier electrically connected to said second output means of said recorder and a third one of at least three input ports of said processor, said fifth isolation transformer the sole said electrical connection between said second output means and said third one of at least three input ports thereby preventing ground loop currents between said recorder and said processor.

* * * * *